(12) United States Patent
Yan

(10) Patent No.: US 6,974,592 B2
(45) Date of Patent: Dec. 13, 2005

(54) ENCAPSULATED AGGLOMERATION OF MICROCAPSULES AND METHOD FOR THE PREPARATION THEREOF

(75) Inventor: Nianxi Yan, Halifax (CA)

(73) Assignee: Ocean Nutrition Canada Limited, Dartmouth (CA)

( * ) Notice: Subject to any disclaimer, the term of this patent is extended or adjusted under 35 U.S.C. 154(b) by 0 days.

(21) Appl. No.: 10/120,621

(22) Filed: Apr. 11, 2002

(65) Prior Publication Data

US 2003/0193102 A1 Oct. 16, 2003

(51) Int. Cl.[7] .......................... A61K 9/14; B32B 15/02; B01J 13/02
(52) U.S. Cl. .......................... 424/489; 264/4.1; 264/4.3; 264/4.32; 264/4.33; 264/4.4; 264/4.7; 428/402.21; 428/402.24; 428/403; 424/492; 424/494; 424/496; 424/497; 424/498
(58) Field of Search .......................... 264/4.1, 4.3, 4.32, 264/4.33, 4.4, 4.7; 428/402.21, 402, 403; 424/489, 492, 494, 496, 497, 498

(56) References Cited

U.S. PATENT DOCUMENTS

| | | | |
|---|---|---|---|
| 2,800,457 A | 7/1957 | Green et al. | 428/402.2 |
| 4,217,370 A | 8/1980 | Rawlings et al. | 426/98 |
| 4,219,439 A | 8/1980 | Miyake et al. | 264/4.4 |
| 4,222,891 A | 9/1980 | Okimoto et al. | 264/4.4 |
| 4,695,466 A | 9/1987 | Morishita et al. | |
| 4,744,933 A | 5/1988 | Rha et al. | |
| 4,749,620 A | 6/1988 | Rha et al. | |
| 4,861,627 A | 8/1989 | Mathiowitz et al. | |
| 4,895,725 A | 1/1990 | Kantor et al. | 424/455 |
| 5,051,304 A | 9/1991 | David et al. | |
| 5,059,622 A | 10/1991 | Sears | 514/549 |
| 5,204,029 A | 4/1993 | Morgan et al. | 264/4.4 |
| 5,456,985 A | 10/1995 | Zgoulli et al. | 428/402.2 |
| 5,573,934 A | 11/1996 | Hubbell et al. | |
| 5,670,209 A | 9/1997 | Wyckoff | |
| 5,766,637 A | 6/1998 | Shine et al. | |
| 5,780,056 A | 7/1998 | Akamatsu et al. | 424/464 |
| 5,827,531 A | 10/1998 | Morrison et al. | |
| 5,993,851 A | 11/1999 | Foldvari | |

(Continued)

FOREIGN PATENT DOCUMENTS

| | | | |
|---|---|---|---|
| EP | 0301777 | 2/1989 | |
| EP | 0 416 575 A | 3/1991 | |
| EP | 1116516 | 7/2001 | |
| GB | 2115768 | 9/1983 | |
| JP | 1148338 | 6/1989 | B01J/13/02 |
| WO | 9211083 | 7/1992 | |
| WO | WO 97/13416 A | 4/1997 | |
| WO | WO 2004/041251 A1 | 5/2004 | |

OTHER PUBLICATIONS

Ijichi et al. (1997) *J. Chem. Eng. Jpn.* 30(5):793–798.
Beestman, George A. Chemical Abstract 2000:793223.
Kage, Hiroyuki, et al. Chemical Abstract 1997:615273.
Yoshida, Masahiro, et al. Chemical Abstract 1990:140735.

*Primary Examiner*—Samuel A. Acquah
(74) *Attorney, Agent, or Firm*—Needle & Rosenberg, P.C.

(57) ABSTRACT

Microcapsules comprising an agglomeration of primary microcapsules, each individual primary microcapsule having a primary shell and the agglomeration being encapsulated by an outer shell, may be prepared by providing an aqueous mixture of a loading substance and a shell material, adjusting pH, temperature, concentration and/or mixing speed to form primary shells of shell material around the loading substance and cooling the aqueous mixture until the primary shells agglomerate and an outer shell of shell material forms around the agglomeration. Such microcapsules are useful for storing a substance and for delivering the substance to a desired environment.

71 Claims, 1 Drawing Sheet

U.S. PATENT DOCUMENTS

| | | |
|---|---|---|
| 6,019,998 A | 2/2000 | Nomoto et al. |
| 6,020,200 A | 2/2000 | Enevold |
| 6,103,378 A | 8/2000 | Yao et al. |
| 6,221,401 B1 | 4/2001 | Zasadzinski et al. ........ 424/490 |
| 6,234,464 B1 | 5/2001 | Krumbholz et al. |
| 6,274,174 B1 | 8/2001 | Hom-ma et al. ............ 424/489 |
| 6,325,951 B1 | 12/2001 | Soper et al. |
| 6,528,165 B2 | 3/2003 | Chandler |
| 6,534,091 B1 | 3/2003 | Garces Garces et al. ... 424/489 |
| 6,534,094 B2 | 3/2003 | Moyano et al. |
| 6,534,926 B1 | 3/2003 | Miller et al. |
| 6,544,926 B1 | 4/2003 | Bodmer et al. |

ENCAPSULATED AGGLOMERATION OF MICROCAPSULES AND METHOD FOR THE PREPARATION THEREOF

FIELD OF THE INVENTION

This invention relates to microcapsules, methods of preparing microcapsules and to their use.

BACKGROUND OF THE INVENTION

Microcapsules are defined as small particles of solids, or droplets of liquids, inside a thin coating of a shell material such as beeswax, starch, gelatine or polyacrylic acid. They are used, for example, to prepare liquids as free-flowing powders or compressed solids, to separate reactive materials, to reduce toxicity, to protect against oxidation and/or to control the rate of release of a substance such as an enzyme, a flavour, a nutrient, a drug, etc.

Over the past fifty years, the prior art has concentrated on so-called "single-core" microcapsules. However, one of the problems with single-core microcapsules is their susceptibility to rupture. To increase the strength of microcapsules, it is known in the art to increase the thickness of the microcapsule wall. However, this leads to a reduction in the loading capacity of the microcapsule. Another approach has been to create so-called "multi-core" microcapsules. For example, U.S. Pat. No. 5,780,056 discloses a "multi-core" microcapsule having gelatine as a shell material. These microcapsules are formed by spray cooling an aqueous emulsion of oil or carotenoid particles such that the gelatine hardens around "cores" of the oil or carotenoid particles. Yoshida et al. (Chemical Abstract 1990:140735 or Japanese patent publication JP 01-148338 published Jun. 9, 1989) discloses a complex coacervation process for the manufacture of microcapsules in which an emulsion of gelatine and paraffin wax is added to an arabic rubber solution and then mixed with a surfactant to form "multi-core" microcapsules. Ijichi et al. (J. Chem. Eng. Jpn. (1997) 30(5):793–798) micoroencapsulated large droplets of biphenyl using a complex coacervation process to form multi-layered mirocapsules. U.S. Pat. No. 4,219,439 and 4,222,891 disclose "multi-nucleus", oil-containing microcapsules having an average diameter of 3–20 $\mu$m with an oil droplet size of 1–10 $\mu$m for use in pressure-sensitive copying papers and heat sensitive recording papers. While some improvement in the strength of microcapsules may be realized by using methods such as these, there remains a need for microcapsules having good rupture strength and good oxidative barrier to the encapsulated substance, preferably in conjunction with high load volumes. Illustrative of this need is the current lack of commercially available 'multicore' microcapsules.

SUMMARY OF THE INVENTION

There is provided a microcapsule comprising an agglomeration of primary microcapsules, each individual primary microcapsule having a primary shell and the agglomeration being encapsulated by an outer shell. There is further provided a process for preparing microcapsules, the process comprising:
(a) providing an aqueous mixture of a loading substance, a first polymer component of shell material and a second polymer component of shell material;
(b) adjusting pH, temperature, concentration, mixing speed or a combination thereof to form shell material comprising the first and second polymer components, the shell material forming primary shells around the loading substance;
(c) cooling the aqueous mixture to a temperature above gel point of the shell material until the primary shells form agglomerations; and,
(d) further cooling the aqueous mixture to form an outer shell of shell material around the agglomerations.

There is still further provided a process for preparing microcapsules, the process comprising:
(a) providing an aqueous mixture of a first polymer component of shell material;
(b) dispersing a loading substance into the aqueous mixture;
(c) then adding a second polymer component of shell material to the aqueous mixture;
(d) adjusting pH, temperature, concentration, mixing speed or a combination thereof to form shell material comprising complex coacervates of the first and second polymer components, the shell material forming primary shells around the loading substance;
(e) cooling the aqueous mixture to a temperature above gel point of the shell material until the primary shells form agglomerations; and,
(f) further cooling the aqueous mixture to form an outer shell of shell material around the agglomerations.

Microcapsules of the present invention may be used to contain a loading substance for a variety of applications.

DETAILED DESCRIPTION

Figure 1:
FIG. 1 is an optical micrograph (400 ×) of encapsulated agglomerations of microcapsules in accordance with the invention.

Composition:

The loading substance may be virtually any substance that is not entirely soluble in the aqueous mixture. Preferably, the loading substance is a solid, a hydrophobic liquid, or a mixture of a solid and a hydrophobic liquid. The loading substance is more preferably a hydrophobic liquid, such as grease, oil or a mixture thereof. Typical oils may be fish oils, vegetable oils, mineral oils, derivatives thereof or mixtures thereof.

The loading substance may comprise a purified or partially purified oily substance such as a fatty acid, a triglyceride or a mixture thereof. Omega-3 fatty acids, such as α-linolenic acid (18:3n3), octadecatetraenoic acid (18:4n3), eicosapentaenoic acid (20:5n3) (EPA) and docosahexaenoic acid (22:6n3) (DHA), and derivatives thereof and mixtures thereof, are preferred. Many types of derivatives are well known to one skilled in the art. Examples of suitable derivatives are esters, such as phytosterol esters, branched or unbranched $C_1$–$C_{30}$ alkyl esters, branched or unbranched $C_2$–$C_{30}$ alkenyl esters or branched or unbranched $C_3$–$C_{30}$ cycloalkyl esters, in particular phytosterol esters and $C_1$–$C_6$ alkyl esters. Preferred sources of oils are oils derived from aquatic organisms (e.g. anchovies, capelin, Atlantic cod, Atlantic herring, Atlantic mackerel, Atlantic menhaden, salmonids, sardines, shark, tuna, etc) and plants (e.g. flax, vegetables, algae, etc). While the loading substance may or may not be a biologically active substance, the microcapsules of the present invention are particularly suited for biologically active substances, for example, drugs, nutritional supplements, flavours or mixtures thereof. Particularly preferred loading substances include antioxidants, such as $CoQ_{10}$ and vitamin E.

The shell material may be any material that can form a microcapsule around the loading substance of interest. The shell material typically comprises at least one polymer component. Examples of polymer components include, but are not limited to, gelatines, polyphosphate, polysaccharides and mixtures thereof. Preferred polymer components are gelatine A, gelatine B, polyphosphate, gum arabic, alginate, chitosan, carrageenan, pectin, carboxy-methylcellulose (CMC) or a mixture thereof. A particularly preferred form of gelatine type A has a Bloom strength of 50–350, more preferably a Bloom strength of 275.

The shell material is preferably a two-component system made from a mixture of different types of polymer components. More preferably, the shell material is a complex coacervate between two or more polymer components. Component A is preferably gelatine type A, although other polymers are also contemplated as component A. Component B is preferably gelatine type B, polyphosphate, gum arabic, alginate, chitosan, carrageenan, pectin, carboxymethyl-cellulose or a mixture thereof. The molar ratio of component A:component B that is used depends on the type of components but is typically from 1:5 to 15:1. For example, when gelatine type A and polyphosphate are used as components A and B respectively, the molar ratio of component A:component B is preferably 8:1 to 12:1; when gelatine type A and gelatine type B are used as components A and B respectively, the molar ratio of component A:component B is preferably 2:1 to 1:2; and when gelatine type A and alginate are used as components A and B respectively, the molar ratio of component A:component B is preferably 3:1 to 5:1.

Processing aids may be included in the shell material. Processing aids may be used for a variety of reasons. For example, they may be used to promote agglomeration of the primary microcapsules, control microcapsule size and/or to act as an antioxidant. Antioxidant properties are useful both during the process (e.g. during coacervation and/or spray drying) and in the microcapsules after they are formed (i.e. to extend shelf-life, etc). Preferably a small number of processing aids that perform a large number of functions is used. For example, ascorbic acid or a salt thereof may be used to promote agglomeration of the primary microcapsules, to control microcapsule size and to act as an antioxidant. The ascorbic acid or salt thereof is preferably used in an amount of about 100 ppm to about 10,000 ppm, more preferably about 1000 ppm to about 5000 ppm. A salt of ascorbic acid, such as sodium or potassium ascorbate, is particularly preferred in this capacity.

Figure 2:
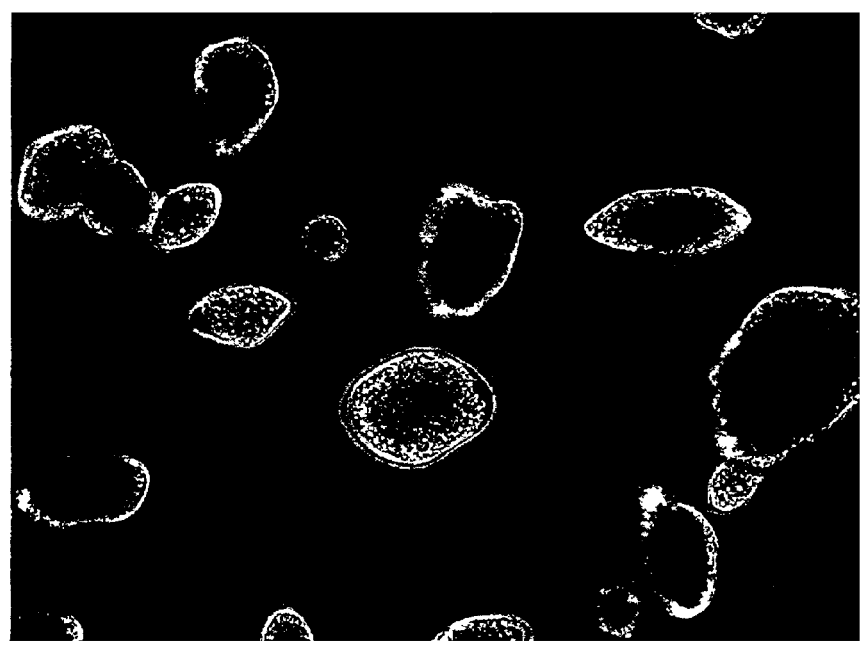
FIG. 2 is a second optical micrograph (400 ×) of encapsulated agglomerations of microcapsules in accordance with the invention.

The structure of encapsulated agglomerations of microcapsules in accordance with the present invention may be seen in FIGS. 1 and 2, which show that smaller (primary) microcapsules have agglomerated together and that the agglomeration is surrounded by shell material to form a larger microcapsule. Each individual primary microcapsule has its own distinct shell called the primary shell. Furthermore, any space that there may be between the smaller microcapsules is filled with more shell material to hold and surround the smaller microcapsules thereby providing an extremely strong outer shell of the larger microcapsule in addition to the primary shell that forms the smaller microcapsules within the larger microcapsule. In one sense, the encapsulated agglomeration of microcapsules may be viewed as an agglomeration of walled bubbles suspended in a matrix of shell material, i.e. a "foam-like" structure. Such an encapsulated agglomeration of microcapsules provides a stronger, more rupture-resistant structure than is previously known in the art, in conjunction with achieving high loads of loading substance.

The primary microcapsules (primary shells) typically have an average diameter of about 40 nm to about 10 $\mu$m, more particularly from about 0.1 $\mu$m to about 5 $\mu$m, even more particularly about 1 $\mu$m. The encapsulated agglomerations (outer shells) may have an average diameter of from about 1 $\mu$m to about 2000 $\mu$m, more typically from about 20 $\mu$m to about 1000 $\mu$m, more particularly from about 20 $\mu$m to about 100 $\mu$m, even more particularly from about 50 $\mu$m to about 100 $\mu$m.

The encapsulated agglomerations of microcapsules prepared by a process of the present invention typically have a combination of payload and structural strength that are better than multi-core microcapsules of the prior art. For example, payloads of loading substance can be as high as about 70% by weight in microcapsules of the present invention having an average size of about 50 $\mu$m for the outer shells and an average size of about 1 $\mu$m for the primary shells.

Process:

In the process for preparing microcapsules, an aqueous mixture of a loading substance, a first polymer component of the shell material and a second polymer component of the shell material is formed. The aqueous mixture may be a mechanical mixture, a suspension or an emulsion. When a liquid loading material is used, particularly a hydrophobic liquid, the aqueous mixture is preferably an emulsion of the loading material and the polymer components.

In a more preferred aspect, a first polymer component is provided in aqueous solution, preferably together with processing aids, such as antioxidants. A loading substance may then be dispersed into the aqueous mixture, for example, by using a homogenizer. If the loading substance is a hydrophobic liquid, an emulsion is formed in which a fraction of the first polymer component begins to deposit around individual droplets of loading substance to begin the formation of primary shells. If the loading substance is a solid particle, a suspension is formed in which a fraction of the first polymer component begins to deposit around individual particles to begin the formation of primary shells. At this point, another aqueous solution of a second polymer component may be added to the aqueous mixture.

Droplets or particles of the loading substance in the aqueous mixture preferably have an average diameter of less than 100 $\mu$m, more preferably less than 50 $\mu$m, even more preferably less than 25 $\mu$m. Droplets or particles of the loading substance having an average diameter less than 10 $\mu$m or less than 5 $\mu$m or less than 3 $\mu$m or less than 1 $\mu$m may be used. Particle size may be measured using any typical equipment known in the art, for example, a Coulter™ LS230 Particle Size Analyzer, Miami, Fla., USA.

The amount of the polymer components of the shell material provided in the aqueous mixture is typically sufficient to form both the primary shells and the outer shells of the encapsulated agglomeration of microcapsules. Preferably, the loading substance is provided in an amount of from about 1% to about 15% by weight of the aqueous mixture, more preferably from about 3% to about 8% by weight, and even more preferably about 6% by weight.

The pH, temperature, concentration, mixing speed or a combination thereof is then adjusted to accelerate the formation of the primary shells around the droplets or particles of the loading substance. If there is more than one type of polymer component, complex coacervation will occur between the components to form a coacervate, which further deposits around the loading substance to form primary shells of shell material. The pH adjustment depends on the type of shell material to be formed. For example, when gelatine type A is a polymer component, the pH may be adjusted to a value from 3.5–5.0, preferably from 4.0–5.0. If the pH of the mixture starts in the desired range, then little or no pH adjustment is required. The initial temperature of the aqueous mixture is preferably set to a value of from about 40° C. to about 60° C., more preferably at about 50° C. Mixing is preferably adjusted so that there is good mixing without breaking the microcapsules as they form. Particular mixing parameters depend on the type of equipment being used. Any of a variety of types of mixing equipment known in the art may be used. Particularly useful is an axial flow impeller, such as Lightnin™ A310 or A510.

The aqueous mixture may then be cooled under controlled cooling rate and mixing parameters to permit agglomeration of the primary shells to form encapsulated agglomerations of primary shells. The encapsulated agglomerations are discrete particles themselves. It is advantageous to control the formation of the encapsulated agglomerations at a temperature above the gel point of the shell material, and to let excess shell material form a thicker outer shell. It is also possible at this stage to add more polymer components, either of the same kind or a different kind, in order to thicken the outer shell and/or produce microcapsules having primary and outer shells of different composition. The temperature is preferably lowered at a rate of 1° C./10 minutes until it reaches a temperature of from about 5° C. to about 10° C., preferably about 5° C. The outer shell encapsulates the agglomeration of primary shells to form a rigid encapsulated agglomeration of microcapsules.

At this stage, a cross-linker may be added to further increase the rigidity of the microcapsules by cross-linking the shell material in both the outer and primary shells and to make the shells insoluble in both aqueous and oily media. Any suitable cross-linker may be used and the choice of cross-linker depends somewhat on the choice of shell material. Preferred cross-linkers are enzymatic cross-linkers (e.g. transglutaminase), aldehydes (e.g. formaldehyde or gluteraldehyde), tannic acid, alum or a mixture thereof. When the microcapsules are to be used to deliver a biologically active substance to an organism, the cross-linkers are preferably non-toxic or of sufficiently low toxicity. The amount of cross-linker used depends on the type of shell material and may be adjusted to provide more or less structural rigidity as desired. For example, when gelatine type A is used in the shell material, the cross-linker may be conveniently used in an amount of about 1.0% to about 5.0%, preferably about 2.5%, by weight of the gelatine type A. In general, one skilled in the art may routinely determine the desired amount in any given case by simple experimentation.

Finally, the microcapsules may be washed with water and/or dried to provide a free-flowing powder. Drying may be accomplished by a number of methods known in the art, such as freeze drying, drying with ethanol or spray drying. Spray drying is a particularly preferred method for drying the microcapsules. Spray drying techniques are disclosed in "Spray Drying Handbook", K. Masters, 5$^{th}$ edition, Longman Scientific Technical UK, 1991, the disclosure of which is hereby incorporated by reference.

Uses:

The microcapsules produced by the process of the present invention may be used to prepare liquids as free-flowing powders or compressed solids, to store a substance, to separate reactive substances, to reduce toxicity of a substance, to protect a substance against oxidation, to deliver a substance to a specified environment and/or to control the rate of release of a substance. In particular, the microcapsules may be used to deliver a biologically active substance to an organism for nutritional or medical purposes. The biologically active substance may be, for example, a nutritional supplement, a flavour, a drug and/or an enzyme. The organism is preferably a mammal, more preferably a human. Microcapsules containing the biologically active substance may be included, for example, in foods or beverages or in drug delivery systems. Use of the microcapsules of the present invention for formulating a nutritional supplement into human food is particularly preferred.

Microcapsules of the present invention have good rupture strength to help reduce or prevent breaking of the microcapsules during incorporation into food or other formulations. Furthermore, the microcapsule's shells are insoluble in both aqueous and oily media, and help reduce or prevent oxidation and/or deterioration of the loading substance during preparation of the microcapsules, during long-term storage, and/or during incorporation of the microcapsules into a formulation vehicle, for example, into foods, beverages, nutraceutical formulations or pharmaceutical formulations.

EXAMPLES

Example 1

54.5 grams gelatine 275 Bloom type A (isoelectric point of about 9) was mixed with 600 grams of deionized water containing 0.5% sodium ascorbate under agitation at 50° C. until completely dissolved. 5.45 grams of sodium polyphosphate was dissolved in 104 grams of deionized water containing 0.5% sodium ascorbate. 90 grams of a fish oil concentrate containing 30% eicosapentaenoic acid ethyl ester (EPA) and 20% docosahexaenoic acid ethyl ester (DHA) (available from Ocean Nutrition Canada Ltd.) was dispersed with 1.0% of an antioxidant (blend of natural flavour, tocopherols and citric acid available as Duralox™ from Kalsec™) into the gelatine solution with a high speed Polytron™ homogenizer. An oil-in-water emulsion was formed. The oil droplet size had a narrow distribution with an average size of about 1 $\mu$m measured by Coulter™ LS230 Particle Size Analyzer. The emulsion was diluted with 700 grams of deionized water containing 0.5% sodium ascorbate at 50° C. The sodium polyphosphate solution was then added into the emulsion and mixed with a Lightning agitator at 600 rpm. The pH was then adjusted to 4.5 with a 10% aqueous acetic acid solution. During pH adjustment and the cooling step that followed pH adjustment, a coacervate formed from the gelatine and polyphosphate coated onto the oil droplets to form primary microcapsules. Cooling was carried out to above the gel point of the gelatine and polyphosphate and the primary microcapsules started to agglomerate to form lumps under agitation. Upon further cooling of the mixture, polymer remaining in the aqueous phase further coated the lumps of primary microcapsules to form an encapsulated agglomeration of microcapsules having an outer shell and having an average size of 50 $\mu$m. Once the temperature had been cooled to 5° C., 2.7 grams of 50% gluteraldehyde was added into the mixture to further strengthen the shell. The mixture was then warmed to room temperature and kept stirring for 12 hours. Finally, the microcapsule suspension washed with water. The washed suspension was then spray dried to obtain a free-flowing powder. A payload of 60% was obtained.

Example 2

Encapsulated agglomerations of microcapsules were formed in accordance with the method of Example 1 except that 0.25% sodium ascorbate was used. A payload of 60% was obtained.

Example 3

Encapsulated agglomerations of microcapsules were formed in accordance with the method of Example 1 except that no ascorbate was used. A payload of 60% was obtained.

Example 4

Encapsulated agglomerations of microcapsules were formed in accordance with the method of Example 1 except that 105 grams of fish oil concentrate was used and a payload of 70% was obtained.

Example 5

Encapsulated agglomerations of microcapsules were formed in accordance with the method of Example 1 except that it was applied to triglyceride (TG) fish oil (available from Ocean Nutrition Canada Ltd.) rather than ethyl ester fish oil.

Example 6

Encapsulated agglomerations of microcapsules were formed in accordance with the method of Example 1 except that gelatine (type A) and gum arabic were used as polymer components of the shell material.

Example 7

Encapsulated agglomerations of microcapsules were formed in accordance with the method of Example 1 except that 150 Bloom gelatine (type A) and polyphosphate were used as polymer components of the shell material and 105 grams of fish oil concentrate was used to obtain a payload of 70%.

Example 8

Encapsulated agglomerations of microcapsules were formed in accordance with the method of Example 1 except that transglutaminase was used to cross-link the shell material.

Example 9 Evaluation of Microcapsules

The microcapsules of Examples 1–8 were evaluated for mechanical strength, encapsulated oil quality and oxidative stability.

Microcapsule shell strength was evaluated by centrifuging a given amount of the prepared microcapsule powders from each of the Examples 1–8 at 34,541 g at 25° C. for 30 minutes in a Sorvall™ Super T-21 centrifuge. The original and the centrifuged powders were washed with hexane to extract oil released from the microcapsules due to shell breakage under centrifuge force. The ratio of percent free oil of the centrifuged powders to that of the original powders is used as an indicator of the shell strength. The lower the ratio, the stronger is the microcapsule's shell.

Oil quality in microcapsules was evaluated by crushing the shells of the prepared microcapsule powders from each of Examples 1–8 with a grinder. The encapsulated oil was then extracted with hexane. Peroxide Value (PV) was analyzed with American Oil Chemist Society Method (AOCS Official Method Cd 8-53: Peroxide value). A high PV indicates a higher concentration of primary oxidation products in the encapsulated oil.

Accelerated oxidative stability was evaluated by placing the prepared microcapsule powders from each of Examples 1–8 in an oxygen bomb (Oxipres™, MIKROLAB AARHUS A/S, Denmark) with an initial oxygen pressure of 5 bar at a constant temperature of 65° C. When the encapsulated fish oil started to oxidize, the oxygen pressure dropped. The time at which the oxygen pressure started to drop is called Induction Period. A longer Induction Period means that the contents of the microcapsules are better protected towards oxidation.

Results are shown in Table 1. The results indicate that the agglomerated microcapsules prepared in accordance with the present invention have excellent strength and resistance to oxidation of the encapsulated loading substance.

TABLE 1

| run # | load (%) | ascorbate (%) | induct period (hr) | PV value | free oil ratio | notes |
|---|---|---|---|---|---|---|
| 1 | 60 | 0.50 | 38 | 3.0 | 2.0 | |
| 2 | 60 | 0.25 | 34 | 4.1 | 1.5 | |
| 3 | 60 | 0.0 | 26 | 7.8 | 1.5 | |
| 4 | 70 | 0.50 | 38 | 3.2 | 1.7 | |
| 5 | 60 | 0.50 | 37 | 0.28 | 3.0 | TG oil |
| 6 | 60 | 0.50 | 30 | 3.4 | 1.5 | gum arabic |
| 7 | 70 | 0.50 | 38 | 4.4 | 2.2 | 150 bloom gelatin |
| 8 | 60 | 0.50 | 33 | 3.2 | 1.1 | enzymatic cross linking |

Other advantages which are obvious and which are inherent to the invention will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

What is claimed is:

1. A microcapsule comprising an agglomeration of primary microcapsules, each individual primary microcapsule having a primary shell and the agglomeration being encapsulated by an outer shell.

2. The microcapsule according to claim 1, wherein the outer shell is a matrix of shell material that surrounds the agglomeration to form a foam-like structure.

3. The microcapsule according to claim 2, wherein the shell material comprises gelatine, polyphosphate, polysaccharide, or a mixture thereof.

4. The microcapsule according to claim 2, wherein the shell material comprises gelatine type A, gelatine type B, polyphosphate, gum arabic, alginate, chitosan, carrageenan, pectin, carboxymethylcellulose or a mixture thereof.

5. The microcapsule according to claim 2, wherein the shell material is a complex coacervate.

6. The microcapsule according to claim 2, wherein the shell material is a complex coacervate between gelatine A and one or more of a polymer component selected from the group consisting of gelatine type B, polyphosphate, gum arabic, alginate, chitosan, carrageenan, pectin and carboxymethylcellulose.

7. The microcapsule according to claim 2, wherein the shell material is a complex coacervate between gelatine A and polyphosphate.

8. The microcapsule according to claim 3, wherein the shell material further comprises an antioxidant.

9. The microcapsule according to claim 8, wherein the antioxidant is ascorbic acid or a salt thereof.

10. The microcapsule according to claim 8, wherein the antioxidant is sodium ascorbate.

11. The microcapsule according to claim 2, wherein the outer shell has an average diameter of from about 1 µm to about 2000 µm.

12. The microcapsule according to claim 2, wherein the outer shell has an average diameter of from about 20 µm to about 1000 µm.

13. The microcapsule according to claim 2, wherein the outer shell has an average diameter of from about 20 µm to about 100 µm.

14. The microcapsule according to claim 2, wherein the outer shell has an average diameter of from about 50 µm to about 100 µm.

15. The microcapsule according to claim 2, wherein the primary shells have an average diameter of from about 40 nm to about 10 µm.

16. The microcapsule according to claim 2, wherein the primary shells have an average diameter of from about 0.1 µm to about 5 µm.

17. The microcapsule according to claim 2, wherein the primary shells have an average diameter of about 1 µm.

18. The microcapsule according to claim 2, having a payload of loading substance of up to about 70% by weight.

19. The microcapsule according to claim 2, wherein the loading substance is a solid, a liquid or a mixture thereof.

20. The microcapsule according to claim 2, wherein the loading substance is grease, oil or a mixture thereof.

21. The microcapsule according to claim 2, wherein the loading substance is a biologically active substance.

22. The microcapsule according to claim 2, wherein the loading substance is a nutritional supplement.

23. The microcapsule according to claim 2, wherein the loading substance is a triglyceride, an omega-3 fatty acid, an ester of an omega-3 fatty acid and/or mixtures thereof.

24. The microcapsule according to claim 2, wherein the loading substance is a phytosterol ester of docosahexaenoic acid and/or eicosapentaenoic acid, a $C_1$–$C_6$ alkyl ester of docosahexaenoic acid and/or eicosapentaenoic acid, and/or a mixture thereof.

25. A process for preparing microcapsules, the process comprising:
   (a) providing an aqueous mixture of a loading substance, a first polymer component of shell material and a second polymer component of shell material;
   (b) adjusting pH, temperature, concentration, mixing speed or a combination thereof to form shell material comprising the first and second polymer components, the shell material forming primary shells around the loading substance;
   (c) cooling the aqueous mixture to a temperature above gel point of the shell material until the primary shells form agglomerations; and,
   (d) further cooling the aqueous mixture to form an outer shell of shell material around the agglomerations.

26. The process according to claim 25, wherein the first polymer component is gelatine type A.

27. The process according to claim 25, wherein the second polymer component is gelatine type B, polyphosphate, gum arabic, alginate, chitosan, carrageenan, pectin, carboxymethylcellulose or a mixture thereof.

28. The process according to claim 25, wherein the second polymer component is polyphosphate.

29. The process according to claim 25, wherein the loading substance is grease, oil or a mixture thereof and is dispersed as an emulsion in the aqueous mixture.

30. The process according to claim 25, wherein the loading substance is a triglyceride, an omega-3 fatty acid, an ester of an omega-3 fatty acid and/or mixtures thereof.

31. The process according to claim 25, wherein the loading substance is provided in an amount of from about 1% to about 15% by weight of the aqueous mixture.

32. The process according to claim 25, wherein an antioxidant is added to the aqueous mixture in part (a).

33. The process according to claim 25, wherein ascorbic acid or a salt thereof is added to the aqueous mixture in part (a).

34. The process according to claim 25, wherein sodium ascorbate is added to the aqueous mixture in part (a).

35. The process according to claim 25, wherein the pH is adjusted to a value from 3.5–5.0.

36. The process according claim 25, wherein the pH is adjusted to a value from 4.0–5.0.

37. The process according to claim 25, wherein the temperature is initially from about 40° C. to about 60° C.

38. The process according to claim 25, wherein the temperature is initially about 50° C.

39. The process according to claim 25, wherein the mixture is cooled at a rate of 1° C./10 minutes.

40. The process according to claim 25, wherein the mixture is cooled until it reaches a temperature of from about 5° C. to about 10° C.

41. The process according to claim 25, wherein the mixture is cooled until it reaches a temperature of about 5° C.

42. The process according to claim 25, further comprising step (g) adding a cross-linker to cross-link the shell material.

43. The process according to claim 42, wherein the cross-linker is an enzymatic cross-linker, an aldehyde, tannic acid, alum or a mixture thereof.

44. The process according to claim 42, wherein the cross-linker is gluteraldehyde.

45. The process according to claim 42, wherein the cross-linker is transglutaminase.

46. The process according to claim 25, further comprising step of drying the microcapsules.

47. A process for preparing microcapsules, the process comprising:
   (a) providing an aqueous mixture of a first polymer component of shell material;
   (b) dispersing a loading substance into the aqueous mixture;
   (c) then adding a second polymer component of shell material to the aqueous mixture;
   (d) adjusting pH, temperature, concentration, mixing speed or a combination thereof to form shell material comprising complex coacervates of the first and second polymer components, the shell material forming primary shells around the loading substance;
   (e) cooling the aqueous mixture to a temperature above gel point of the shell material until the primary shells form agglomerations; and,
   (f) further cooling the aqueous mixture to form an outer shell of shell material around the agglomerations.

48. The process according to claim 47, wherein the first polymer component is gelatine type A.

49. The process according to claim 47, wherein the second polymer component is gelatine type B, polyphosphate, gum arabic, alginate, chitosan, carrageenan, pectin, carboxymethylcellulose or a mixture thereof.

50. The process according to claim 47, wherein the second polymer component is polyphosphate.

51. The process according to claim 47, further comprising adding more polymer components to the aqueous mixture in part (e).

52. The process according to claim 47, wherein the loading substance is grease, oil or a mixture thereof and is dispersed as an emulsion in the aqueous mixture.

53. The process according to claim 47, wherein the loading substance is a triglyceride, an omega-3 fatty acid, an ester of an omega-3 fatty acid and/or mixtures thereof.

54. The process according to claim 47, wherein the loading substance is provided in an amount of from about 1% to about 15% by weight of the aqueous mixture.

55. The process according to claim 47, wherein an antioxidant is added to the aqueous mixture in part (a).

56. The process according to claim 47, wherein ascorbic acid or a salt thereof is added to the aqueous mixture in part (a).

57. The process according to claim 47, wherein sodium ascorbate is added to the aqueous mixture in part (a).

58. The process according to claim 47, wherein the pH is adjusted to a value from 3.5–5.0.

59. The process according claim 47, wherein the pH is adjusted to a value from 4.0–5.0.

60. The process according to claim 47, wherein the temperature is initially from about 40° C. to about 60° C.

61. The process according to claim 47, wherein the temperature is initially about 50° C.

62. The process according to claim 47, wherein the mixture is cooled at a rate of 1° C./10 minutes.

63. The process according to claim 47, wherein the mixture is cooled until it reaches a temperature of from about 5° C. to about 10° C.

64. The process according to claim 47, wherein the mixture is cooled until it reaches a temperature of about 5° C.

65. The process according to claim 47, further comprising step (g) adding a cross-linker to cross-link the shell material.

66. The process according to claim 65, wherein the cross-linker is an enzymatic cross-linker, an aldehyde, tannic acid, alum or a mixture thereof.

67. The process according to claim 65, wherein the cross-linker is gluteraldehyde.

68. The process according to claim 65, wherein the cross-linker is transglutaminase.

69. The process according to claim 47, further comprising step of drying the microcapsules.

70. Microcapsules prepared by a process according to claim 25.

71. Microcapsules prepared by a process according to claim 47.

* * * * *